United States Patent
Quackenbush

(10) Patent No.: US 11,147,905 B2
(45) Date of Patent: *Oct. 19, 2021

(54) BREAST PUMP

(71) Applicant: MOMI BRANDS, INC., Winston Salem, NC (US)

(72) Inventor: Carr Lane Quackenbush, Monson, MA (US)

(73) Assignee: MOMI BRANDS, INC., Winston Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/060,302

(22) Filed: Oct. 1, 2020

(65) Prior Publication Data

US 2021/0069391 A1 Mar. 11, 2021

Related U.S. Application Data

(60) Continuation-in-part of application No. 16/251,198, filed on Jan. 18, 2019, now Pat. No. 10,806,837.
(Continued)

(51) Int. Cl.
*A61M 1/06* (2006.01)
*A61M 39/24* (2006.01)

(52) U.S. Cl.
CPC ............ *A61M 1/064* (2014.02); *A61M 39/24* (2013.01); *A61M 2205/3344* (2013.01)

(58) Field of Classification Search
CPC ........ A61M 1/064; A61M 1/06; A61M 1/062; A61M 1/066; A61M 1/068; A61M 39/24; A61M 2205/3344
See application file for complete search history.

(56) References Cited

U.S. PATENT DOCUMENTS 2,864,628 A 12/1958 Edleson
4,607,596 A 8/1986 Whittlestone et al.
(Continued)

FOREIGN PATENT DOCUMENTS

CA 2240268 A1 12/1999
WO 2004/058330 A1 7/2004

OTHER PUBLICATIONS

International Search Report for International Application No. PCT/US2017/68633 dated Mar. 19, 2018.
(Continued)

*Primary Examiner* — Rebecca E Eisenberg
*Assistant Examiner* — John A Doubrava
(74) *Attorney, Agent, or Firm* — Lathrop GPM LLP; Wm. Tucker Griffith

(57) ABSTRACT

A pump apparatus and method for extracting breastmilk is disclosed. A pump head comprises a funnel-shaped breast shield portion and a neck portion leading to a collection container. A deformable elastic component is sealed within an opening formed in the neck portion and manipulated to engage the user's nipple to simulate the suckling of an infant. The deformable elastic component is configured to move into the interior volume of the neck portion under an applied positive pressure to compress the nipple and control nipple edema. The deformable elastic component is also configured to move away from the axial center of the neck portion under an applied negative pressure to create suction and extract breastmilk in a manner that closely replicates the suckling of an infant. The pump may also include another deformable elastic component to stimulate a Milk Ejection Reflex (MER).

22 Claims, 6 Drawing Sheets

Related U.S. Application Data which is a continuation of application No. 16/004,742, filed on Jun. 11, 2018, now Pat. No. 10,286,130, which is a division of application No. 15/403,578, filed on Jan. 11, 2017, now Pat. No. 10,016,548.

(56) References Cited

U.S. PATENT DOCUMENTS

| | | | |
|---|---|---|---|
| 4,857,051 | A | 8/1989 | Larsson |
| 6,673,036 | B1 | 1/2004 | Britto |
| 6,749,582 | B2 | 6/2004 | Britto et al. |
| 6,840,918 | B1 | 1/2005 | Britto et al. |
| 6,887,210 | B2 | 5/2005 | Quay |
| 7,875,000 | B2 | 1/2011 | Krebs et al. |
| 7,988,661 | B2 * | 8/2011 | Silver ............ A61M 1/064 604/74 |
| 8,052,635 | B1 | 11/2011 | Kelly |
| 8,118,772 | B2 | 2/2012 | Dao et al. |
| 8,216,179 | B2 | 7/2012 | Bosshard et al. |
| 8,961,454 | B2 | 2/2015 | Chen |
| 10,016,548 | B1 * | 7/2018 | Quackenbush ....... A61M 1/064 |
| 10,286,130 | B2 | 5/2019 | Quackenbush |
| 10,806,837 | B2 * | 10/2020 | Quackenbush ....... A61M 39/24 |
| 2004/0158199 | A1 | 8/2004 | McKendry et al. |
| 2006/0106334 | A1 | 5/2006 | Jordan |
| 2014/0121593 | A1 | 5/2014 | Felber et al. |
| 2014/0288466 | A1 | 9/2014 | Alvarez et al. |
| 2014/0378946 | A1 | 12/2014 | Thompson |
| 2015/0065994 | A1 | 3/2015 | Fridman et al. |
| 2016/0000982 | A1 | 1/2016 | Alvarez et al. |
| 2016/0058928 | A1 | 3/2016 | Nowroozi et al. |
| 2016/0206794 | A1 | 7/2016 | Makower et al. |
| 2019/0240386 | A1 * | 8/2019 | Larsson ............ A61M 1/066 |

OTHER PUBLICATIONS

Written Opinion for International Application No. PCT/US2017/68633 dated Mar. 19, 2018.

N.P. Aleekseev, E.V. Omel'yanyuk, and N.E. Talalaeva, Dynamics of milk ejection reflexes accompanying continuous rhythmic stimulation of the areola—nipple complex of the mammary gland, 2000, Ros. Fiziol, Zhum, im. I.M. Sechenova, vol. 86, No. 6, pp. 711-719 (Year: 2000).

* cited by examiner

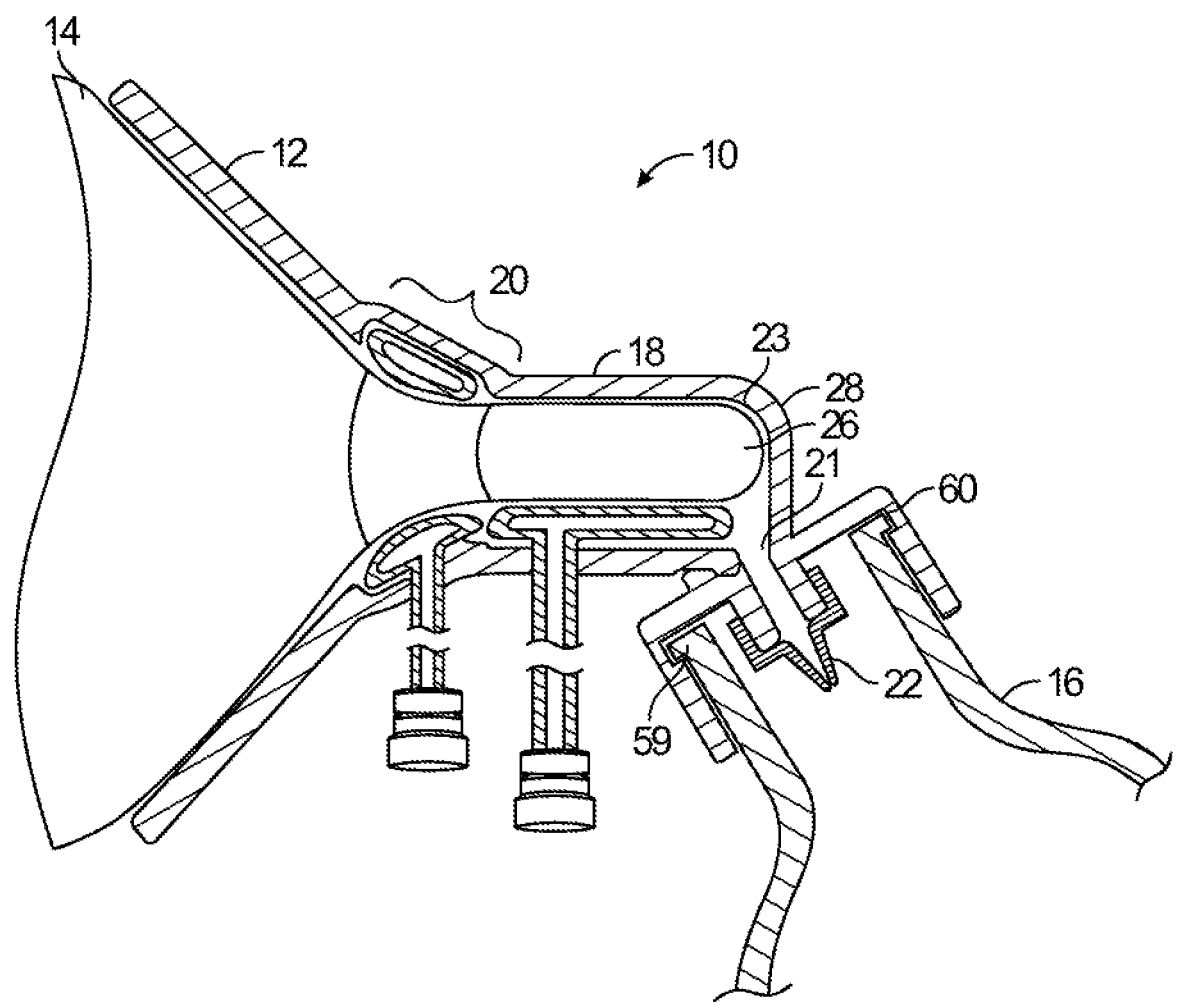
FIG. 1B
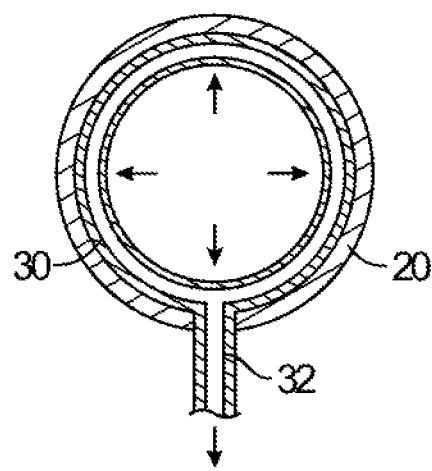 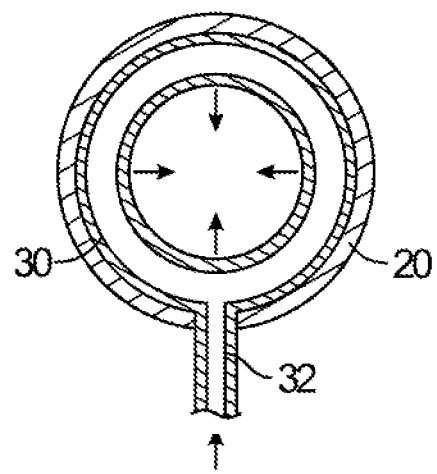
FIG. 2A  FIG. 2B

BREAST PUMP

CROSS-REFERENCE TO RELATED APPLICATIONS

This application is a continuation-in-part of U.S. patent application Ser. No. 16/251,198, filed Jan. 18, 2019, which is a continuation of U.S. patent application Ser. No. 16/004,742, filed Jun. 11, 2018, issued as U.S. Pat. No. 10,286,130, which is a divisional of U.S. patent application Ser. No. 15/403,578, filed Jan. 11, 2017, issued as U.S. Pat. No. 10,016,548, each of which is hereby incorporated by reference in its entirety.

FIELD OF INVENTION

The present invention relates generally to milking and breast pump devices and, more particularly, to breast pumps for lactating females designed to mimic the natural suckling action of an infant during breast-feeding.

BACKGROUND OF THE INVENTION

Newborns and infants experience immediate and long-term benefits from breast milk feeding that are well documented. (See Cunningham A. S., Jelliffe D. B., Jelliffe E. F., Breast feeding and health in the 1980s: a global epidemiological review. Journal of Pediatrics. 1991, 118: 659-666). These benefits include providing protection against many illnesses caused by allergies, bacteria and viruses, such as stomach viruses, respiratory illnesses, ear infections, meningitis and the like. (See Fallot M. E., Boyd J. L., Oski F. A., Breast-feeding reduces incidence of hospital admissions for infection in infants. Pediatrics. 1980, 65:1121-1124). Breast milk feeding also may increase intelligence and fight obesity.

Nursing mothers may desire to impart the above-noted benefits of breast milk to their infant when the two are separated. Additionally, traditional nursing may not be possible or convenient at all times and locations. Thus, to extract breast milk to later feed to the infant, nursing mothers can use a breast pump. The extracted breast-milk can be fed to the infant using a bottle fitted with an artificial teat.

In order to remove milk, a milk ejection reflex (MER) must first occur. The mechanism to initiate an MER is not precisely understood and is not always readily reproduced with available commercial breast pumps.

All commercial electric breast pumps use vacuum (negative air pressure) applied to the mother's breasts to extract milk. Such devices are typically large, loud and energy-inefficient, compromising discretion and portability. Moreover, vacuum to extract breast milk is completely different than the suckling action of the infant; in which the infant's mouth is filled only with liquid, no air. Worse still, breast pumps using only vacuum can cause significant pain or even edema in nursing mothers.

Therefore, it is desirous to provide an improved approach to breast pumps that more closely mimics the natural suckling action of the infant, is discrete in use and does not cause pain or edema.

SUMMARY OF THE INVENTION

The present invention provides a breast pump that more closely mirrors the natural suckling action of an infant, and as a result improves upon the collection of breast-milk generally associated with breast pumps.

According to a first aspect of the present invention, a device for extracting breast-milk from a breast comprises an external shell for a pump head that includes a funnel-shaped portion configured to receive and seal against the breast, a neck portion extending from the funnel-shaped portion and defining a proximal end and a distal end, said neck portion being adapted to receive and position a nipple of the breast, a feed channel defined at the distal end of the neck portion, a one-way check valve disposed along the feed channel, and a deformable elastic component being adapted for alternating expansion and contraction and having a first surface facing into the neck portion. The deformable elastic component is configured to contract under applied negative pressure below the atmospheric pressure to create a volume external to the deformable elastic component, around and in front of the nipple, to create suction, elongate the nipple and extract breastmilk, wherein the one-way check valve is closed by the suction so that extracted breastmilk collects in the feed channel. The deformable elastic component is also configured to expand under applied positive pressure above atmospheric pressure to compress the nipple against an opposing solid interior surface of the neck portion to control nipple edema, wherein the expansion of the deformable elastic component pushes breastmilk through the one-way check valve.

In preferred embodiments, the first surface of the deformable elastic component, where the "first" surface of the deformable elastic component is the surface facing into the neck component, is configured to deform into an interior volume of the neck portion when positive pressure is applied to the component such that the first surface of the component compresses the nipple against the opposing interior solid surface of the neck portion to control nipple edema. Further, the first surface of the deformable elastic component is configured to deform away from the interior of the neck portion when negative pressure is applied to the component so as to create a volume within the neck portion, external to the component, around and in front of the nipple, to create suction and extract breastmilk.

In preferred embodiments, the neck portion includes an opening in which the deformable elastic component is seated and sealed. As positioned in said opening, the first surface of the deformable elastic component preferably extends across the opening. Still further, the deformable elastic component is preferably hermetically sealed into the neck portion. Preferably, the first surface of the deformable elastic component is shaped so that, without deflection, said first surface and an interior surface of the neck portion adjacent thereto form a generally unobstructed cavity within the pump head to receive and position the nipple of the breast.

In embodiments of the present invention, the deformable elastic component comprises a single unitary, hermetic unit. In alternate embodiments, the deformable elastic component is composed of multiple components, sealed together, and configured to function as a single unitary, hermetic unit. The deformable elastic component can comprise a bladder, a hollow capsule, or the like, sealingly mounted relative to an opening in the neck portion of the external shell of the pump head. The deformable elastic component can be filled with air, a gas, a liquid, a gel, or the like, and be manipulated under pressure, including using a pump (hydraulic, pneumatic, electric or manual). For example, in preferred embodiments, the device can include a pump to actuate or deform the deformable elastic components, and, if there are two such components, a valve switch to select which component is to be activated. The deformable elastic component may be bonded into the pump head or may be detachable.

In embodiments of the present invention, a collection container can be provided to collect extracted breastmilk, wherein the collection container is located downstream of the one-way valve. In preferred embodiments, the collection container is attachable to a connection portion, preferably threaded, formed on the feed channel of the pump head device to form a seal serving to prevent breastmilk leakage from the collection container when the pump head is tipped. An air vent may further be provided to allow the release of air from the collection container as breastmilk is pumped into said container. In preferred embodiments, the air vent is located at a position upstream from the connection portion at a high point to reduce likelihood that breastmilk will leak through the air vent when the pump head is tipped.

In embodiments of the present invention, a second deformable elastic component, capable of expansion and contraction, can be provided and configured to initiate a Milk Ejection Reflex (MER) aka a "let down", is disposed within the device.

According to another aspect of the present invention, a device for extracting breastmilk from a breast comprises an external shell for a pump head that includes a funnel-shaped portion configured to receive and seal against the breast, a neck portion extending from the funnel-shaped portion and defining a proximal end and a distal end, said neck portion being adapted to receive and position a nipple of the breast, and a feed channel defined at the distal end of the neck portion. A first deformable elastic component is adapted for alternating expansion and contraction and has a first surface facing into the neck portion. A second deformable elastic component configured to initiate a Milk Ejection Reflex (MER) is adapted for expansion and contraction and disposed within the device. The first deformable elastic component is configured to contract under applied negative pressure below the atmospheric pressure to create a volume external to the deformable elastic component, around and in front of the nipple, to create suction, elongate the nipple and extract breastmilk. The first deformable elastic component is also configured to expand under applied positive pressure above atmospheric pressure to compress the nipple against an opposing solid interior surface of the neck portion to control nipple edema.

According to the present invention, a method of extracting milk includes providing a pump head with an expandable and contractible first deformable elastic component, and an expandable and contractible second deformable elastic component, providing a hydraulic pump with a valve switch, which connects the hydraulic pump to either the first deformable elastic component through the valve switch via a first tube or to the second deformable elastic component through the valve switch via a second tube, inserting a breast into the pump head, turning the connected pump head and hydraulic pump to an on position, initiating a stimulation phase by the hydraulic pump delivering fluid to the second deformable component, expanding and contracting the second deformable component against and away from the breast, then, after a pre-set period of time or sooner if the user desires, switching the valve switch to deliver fluid to the first deformable component, compressing a nipple of the breast, and collecting milk excreted from the nipple via a feed channel and through the check valve.

According to another embodiment of the present invention, a method of extracting milk includes providing a pump head with an expandable and contractible first deformable elastic component having a first surface facing an interior of the pump head, contracting the first deformable elastic component under applied negative pressure below the atmospheric pressure to create a volume external to the first deformable elastic component, around and in front of the nipple, to create suction, to elongate the nipple and to extract breastmilk, and expanding the first deformable elastic component under applied positive pressure above atmospheric pressure to compress the nipple against an opposing solid interior surface of the neck portion to control nipple edema. When negative pressure is applied to the first deformable elastic component, the first surface of the first deformable elastic component moves away from the interior of the neck portion of the pump head so as to create a volume within the neck portion, external to the first deformable elastic component, around and in front of the nipple, to create suction and to extract breastmilk. When positive pressure is applied to the first deformable elastic component, the first surface of the first deformable elastic component moves into the interior volume of the neck portion of the pump head such that the first surface compresses the nipple against the opposing solid interior surface of the neck portion to control nipple edema. In embodiments of the present invention including a one-way check valve in the pump head, said check valve is closed by the suction created by contraction of the first deformable elastic component so that extracted breastmilk collects in a feed channel, and further wherein the expansion of the first deformable elastic component pushes breastmilk through the one-way check valve for collection in a collection container.

In another aspect of the present invention, the device for extracting milk can comprise a hydraulic milking machine.

These and other objects, features and advantages of the present invention will become apparent in light of the detailed description of embodiments thereof, as illustrated in the accompanying drawings.

BRIEF DESCRIPTION OF THE DRAWINGS

FIG. 1B is a cross section view of a breast inserted within the breast pump head of FIG. 1A, in accordance with embodiments of the present invention.

FIG. 2A is a cross section view taken across line A-A of FIG. 1A showing the receiver section and the second deformable elastic component of FIG. 1A when deflated, in accordance with embodiments of the present invention.

FIG. 2B is a cross section view taken across line A-A of FIG. 1A showing the receiver section and the second deformable elastic component of FIG. 1A when inflated, in accordance with embodiments of the present invention.

DETAILED DESCRIPTION OF PREFERRED EMBODIMENTS

The following descriptions of the figures will convey details of construction and operation of a breast pump in accordance with the present invention.

As described herein, the term "vacuum" is used to connote negative air pressure, i.e. air pressure below atmospheric, whereas "suction" is used to connote negative pressure, i.e. pressure below atmospheric, in air-filled or liquid-filled systems. The term "positive pressure" is used to connote fluid pressure, air or liquid, above atmospheric pressure. "Expandable", "inflate", "inflated", "inflating", or similar terms, are used to connote an increase in size caused by applying positive fluid pressure to a capsule or bladder, i.e. pumping fluid into the capsule or bladder. "Contractible", "deflate", "deflated", "deflating", or similar terms, are used to connote a decrease in size caused by applying negative fluid pressure to a capsule or bladder, i.e., removing fluid from the capsule or bladder.

Additionally, "proximal" and "distal" are used in their medical sense and directionally with respect to the user. Thus, "distal" is farthest from the user, and the "distal portion" of the nipple is the portion drawn deepest into the pump. "Bottom," "lower" or "down" signify a direction toward the milk collection container. Conversely, "top," "upper" or "up" refer to a direction away from the milk collection container. "Inward" refers to a direction towards the axial centerline of the neck portion of the pump head.

Figure 1A:
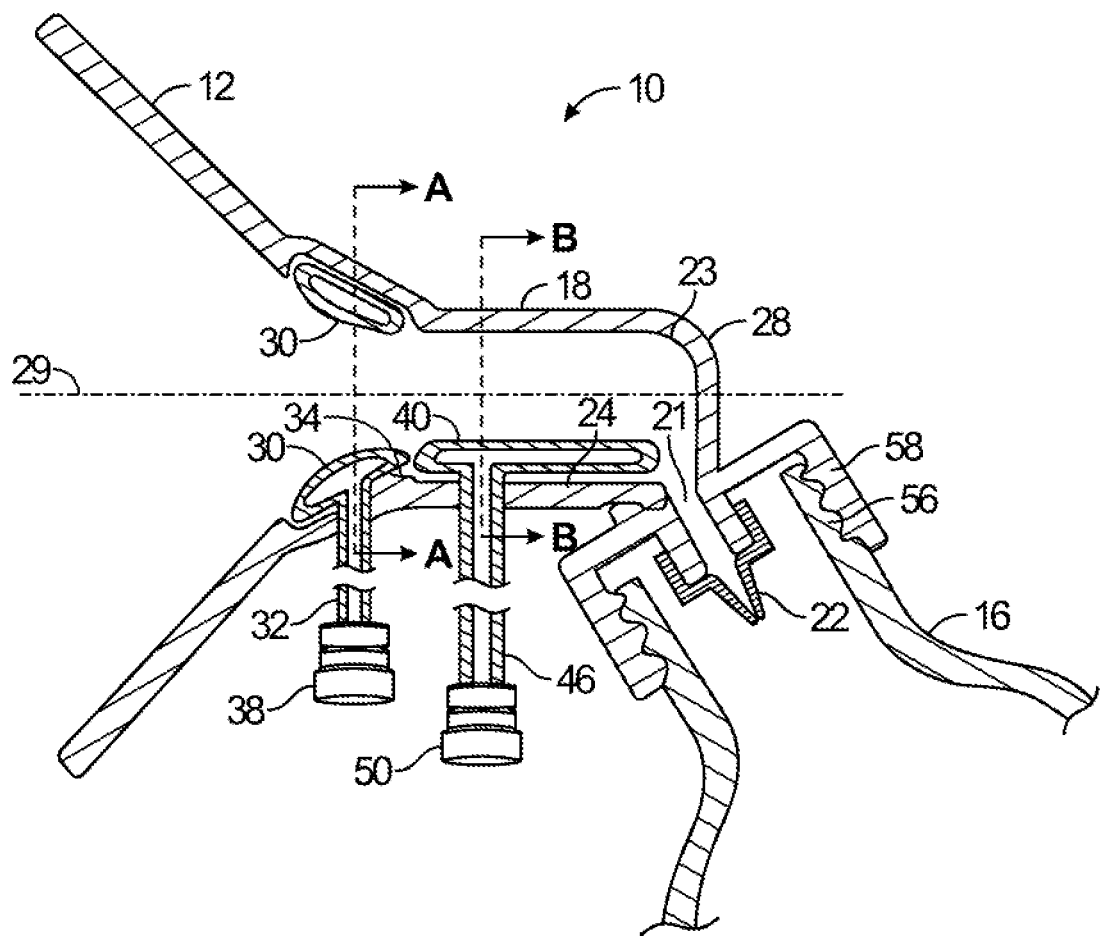
FIG. 1A is a cross section view of a breast pump head including a funnel-shaped breast shield section, a first deformable elastic component, a receiver section, a second deformable elastic component, and a milk collection container, in accordance with embodiments of the present invention.

Referring to FIGS. 1A and 1B, an assembled pump head 10 for extracting milk includes a funnel-shaped breast shield portion 12 sealably connecting a breast 14 to a collection container 16 through a distally curved and hollow receiver neck portion 18. As illustrated, the funnel-shaped breast shield portion 12 narrows to the receiver neck portion 18 through a transition portion 20. The receiver neck portion 18 includes a proximal end located adjacent to the transition portion 20 and a distal end positioned away from the transition portion 20 and the funnel-shaped breast shield portion 12. Preferably, the distal end of the receiver neck portion 18 is closed off so that the channel formed within the pump head 10 feeds to a feed channel 21. In operation, when a breast 14 is placed in the pump head 10 to extract milk, the milk will feed through this feed channel 21 then though a one-way check valve 22 to be collected in the collection container 16.

The receiver neck portion 18 includes a top surface 23 and a bottom interior surface 24 forming a hollow and nominally cylindrical area adapted to receive a nipple 26 when the user's breast is inserted into the pump head 10. The receiver neck portion 18 further includes a downward curving portion 28 at its distal end. Specifically, the downward curving portion 28 curves at an angle of approximately ninety to one hundred and forty-degrees relative to a longitudinal axis 29 of the receiver neck portion 18. The entire interior surface of the receiver portion 18, including the downward curving portion 28, is smooth to prevent surface imperfections from irritating the nipple 26 and shaped to not inhibit milk collection.

In embodiments of the present invention, an annular second deformable elastic component 30 is illustrated in FIGS. 1A, 1B, 2A and 2B as an annular unitary and hermetic deformable elastic component that may also comprise a composite, hermetic deformable elastic component composed of multiple components sealed together to act as a unitary component. As apparent to those skilled in the art other configurations are possible without departing from the spirit of the concept. The second deformable elastic component 30 is configured to mechanically stimulate the breast 14 is disposed within the assembled pump head 10. More specifically, the second deformable elastic component 30 is disposed at the transition portion 20, where the breast shield portion 12 meets the receiver neck portion 18 and extends around the entire inner circumference/perimeter as shown in FIGS. 2A and 2B. Additionally, the second deformable elastic component 30 is an expandable bladder filled with air or liquid for providing pulsating compression to the breast 14, specifically the areola region. In alternative embodiments, the second deformable elastic component 30 may only partially cover the circumference of the funnel-shaped breast shield portion 12 and/or receiver neck portion 18 forming a "C" or "U" shape. Thus, in operation, only bottom, top, side, or angled compression may be applied to an areola region of the breast 14 by the second deformable elastic component 30.

To maintain position, prevent milk leakage, and facilitate cleaning, the second deformable elastic component 30 may be bonded over the entire surface of the transition portion 20 where the second deformable elastic component 30 touches the funnel breast shield portion 121 receiver neck portion 18 surfaces. Extending outward from the second deformable elastic component 30 and externally away from the pumping head 10 is a second tube or nozzle 32 that, as illustrated in FIG. 1A, passes through a lower interior surface 34 of the pump head assembly 10 to a second pump tube (shown as reference numeral 36 in FIG. 6). In embodiments, a second leak-proof disconnect 38 may be disposed between the second tube 32 and the second pump tube 36.

Figure 4:
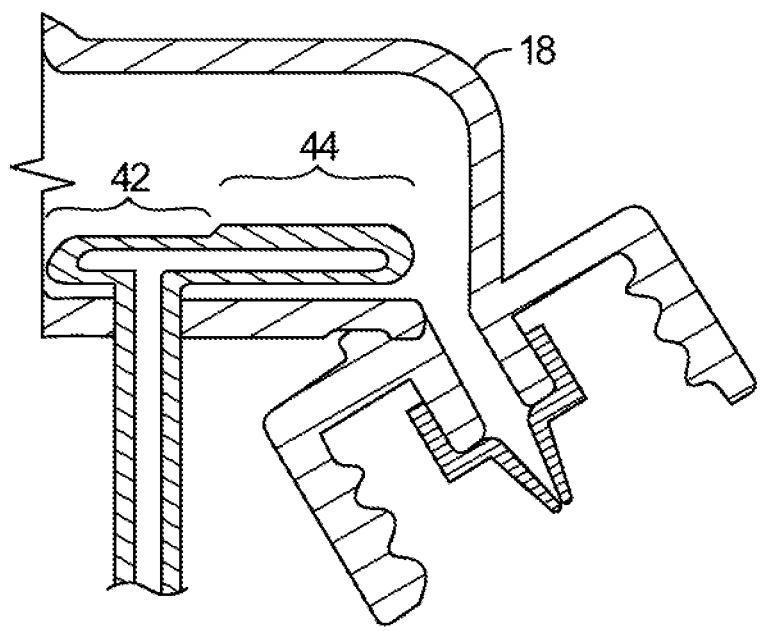
FIG. 4 is an enlarged view of the receiver section of FIG. 1A including a first deformable elastic component in accordance with another embodiment of the present invention.

Disposed along the bottom interior surface of the receiver neck portion 18 is a first hermetic deformable elastic component 40 configured to inflate and deflate, and thus expand and contract within the pump head 10. In some embodiments, the first deformable elastic component 40 is an expandable capsule filled with air, liquid or gel, and has a uniform top thickness. In other embodiments, such as shown in FIG. 4, a proximal section 42 of the top surface of the first deformable elastic component 40 is thinner than a distal section 44 of the top surface.

Figure 6:
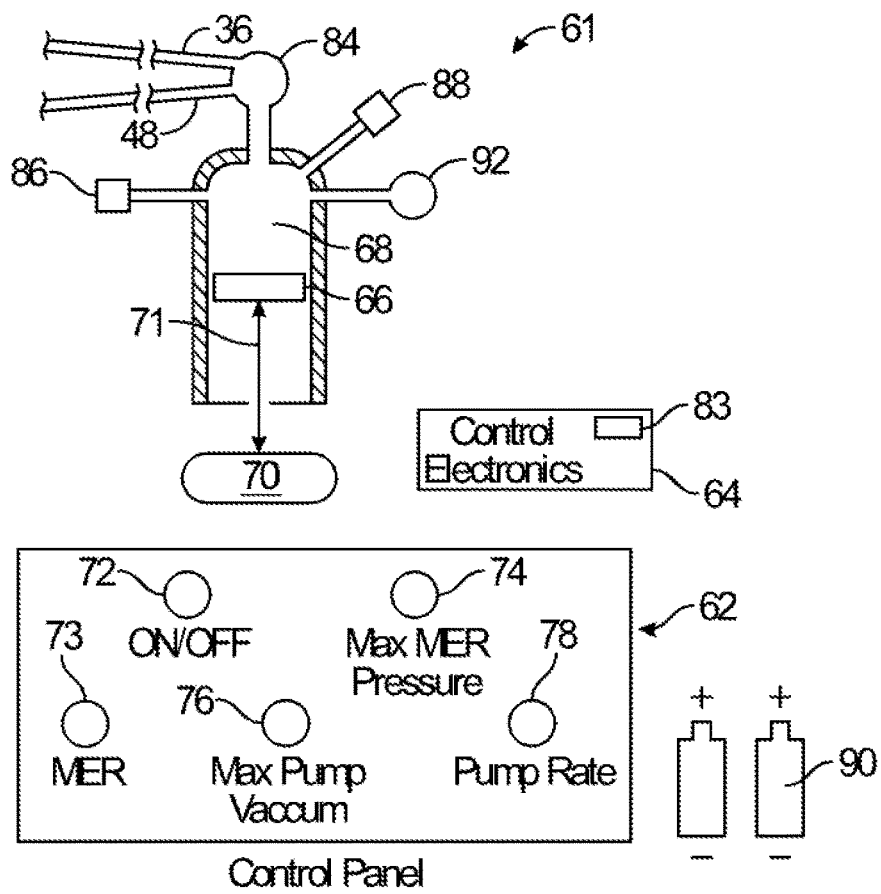
FIG. 6 is a schematic illustration of a pump including a motor, control electronics, various sensors, control elements and control panel, in accordance with embodiments of the present invention.

Referring back to FIGS. 1A and 1B, extending outward from the first deformable elastic component 40 and externally away from the pump head 10 is a first tube or nozzle 46 that, as illustrated, passes through the lower interior surface 34 of the pump head assembly 10 to a first pump tube (shown as reference numeral 48 in FIG. 6). In embodiments, a first leak-proof disconnect 50 may be disposed between the first tube 46 and first pump tube 48. The two leak-proof disconnects 38, 50 may be situated anywhere along the tubes 32, 46, connecting respectively to pump tubes 36 and 48 in FIG. 6, running from the pump head 10.

The downward curving portion 28 leads into feed channel 21, which leads to the check valve 22 and then into the collection container 16 which can be a bottle, a bag, or a similar device for collecting extracted milk. Specifically, the feed channel 21 is located above the check valve 22. The check valve 22 is normally-closed and configured to allow milk to enter the collection container 16 while preventing air from leaking into the feed channel 21 which would compromise liquid fill in the pump head 10. In some embodiments, the check valve 22 is a duck-billed valve, although other one-way valves are also contemplated.

The collection container 16 may contain external threads 56 corresponding to a female threaded collar 58 of the pump head 10 for removably connecting the collection container 16. In some embodiments, the collection container contains female threads while the pump head collar 58 has external threads. Other means for connecting the collection container 16 to the pump head 10 are also contemplated, such as snapping the collection container 16 with a flexibly formed top 59 into a recessed grove 60, as shown in FIG. 1B. The threaded connection of the collection container 16 to the collar 58 forms a seal serving to prevent breastmilk leakage from the collection container 16 when the pump head 10 is tipped. An air vent may further be provided to allow the release of air from the collection container 16 as breastmilk is pumped into said container 18. In preferred embodiments, the air vent is located at a position upstream from the collar 58 to reduce likelihood that breastmilk will leak through the air vent when the pump head 10 is tipped.

Referring to FIGS. 2A and 2B, a cross-section of the transition portion 20 across line A-A in FIG. 1A is shown.

The overall cross-section of the transition portion 20 is substantially circular as the funnel-shaped shield portion 12 narrows to the hollow receiver neck portion 18. As discussed in connection with FIG. 1A, the annular second deformable elastic component 30 extends completely or partially around the inner circumference/perimeter of the funnel-shaped shield portion 12, transition portion 20 and/or receiver portion 18. When the second deformable elastic component 30 is deflated, the aperture through the funnel-shaped shield portion 12, transition portion 20 and/or receiver portion 18 is larger than when the second deformable elastic component 30 is inflated.

Figure 3:
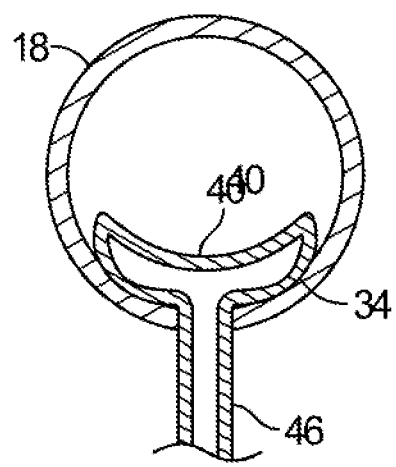
FIG. 3 is a cross section view taken across line B-B of FIG. 1A showing the receiver section and the deflated first deformable elastic component of FIG. 1A, in accordance with embodiments of the present invention.

Referring to FIG. 3, a cross-section of the receiver neck portion 18 across line B-B in FIG. 1A is shown with the first deformable elastic component 40 substantially deflated.

The overall cross-section of the receiver neck portion 18 is substantially round such that the neck portion 18 generally forms a nominally cylindrical tube, although it may have other shapes, for example oval or tapered. For positioning, to prevent milk leakage and to facilitate cleaning, the first deformable elastic component 40 may be bonded where it touches the lower interior surface 34 and generally extend along the bottom interior surface 24 of the tubular neck portion 18. It may also be recessed into a pocket in the tubular neck portion 18. In embodiments, and as pictured in FIG. 3, a fully deflated first deformable elastic component 40 maintains the substantially round internal cross-section of the receiver neck portion 18. In alternative embodiments, when inflated, the first deformable elastic component 40 may sufficiently occupy the interior distal portion of the receiver neck portion 18 such that compression may be applied to the nipple 26 by the first deformable elastic component 40 so that the nipple 26 is completely compressed against the top interior of the neck portion 18. These inflations and deflations of the first deformable elastic component 40 are intended to mimic the natural suckling action of an infant.

Referring to FIG. 4, an enlarged view of the receiver neck portion 18 of FIG. 1A including a first deformable elastic component 40 in accordance with an embodiment of the present invention is shown. The proximal section 42 of the top surface of the first deformable elastic component 40 is thinner than the distal section 44 of the top surface. The thinner proximal section 42 allows it to stretch more easily than the thicker distal section 44 which is stiffer and so more difficult to stretch. Thus, when the first deformable elastic component 40 is expanding, the proximal section 42 will rise in advance of the distal section 44. When the first deformable elastic component 40 is contracting, the proximal section 42 will remain in an elevated position longer relative to the distal section 44. This operation is pictured in FIGS. 5A-5C.

Figure 5A:
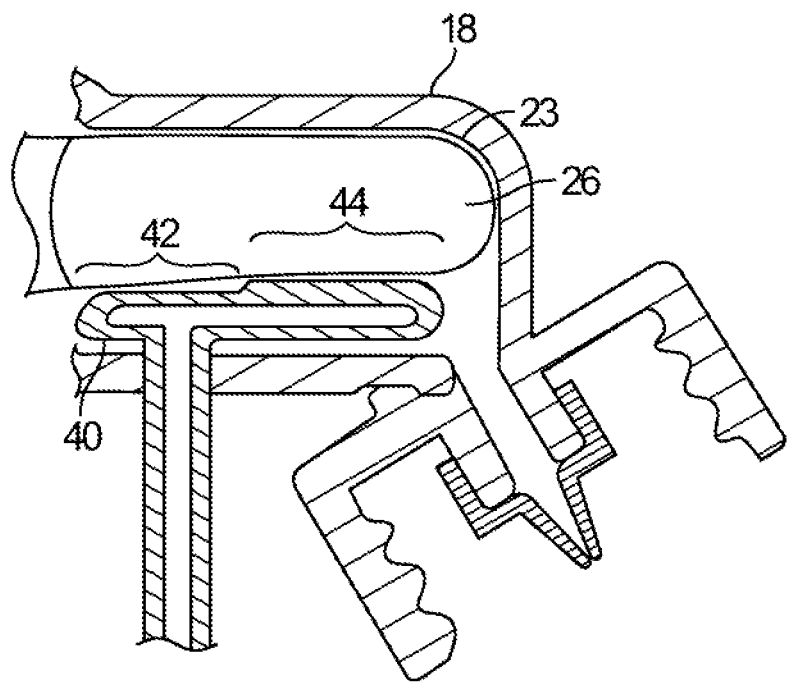
FIG. 5A is a cross section view of the first deformable elastic component of FIG. 4 in a fully deflated initial position, in accordance with embodiments of the present invention.
Figure 5B:
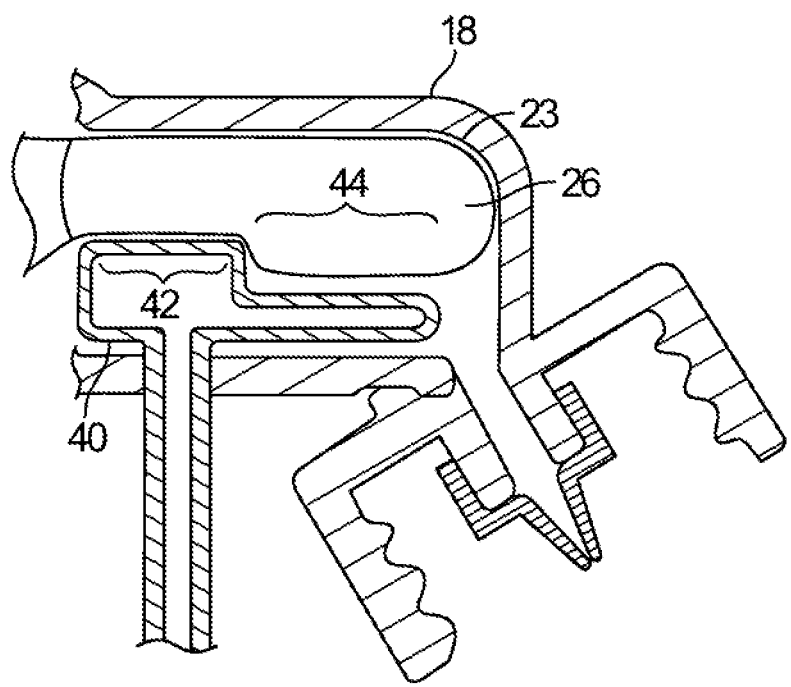
FIG. 5B is a cross section view of the first deformable component of FIG. 4 at a slightly inflated configuration, in accordance with embodiments of the present invention.
Figure 5C:
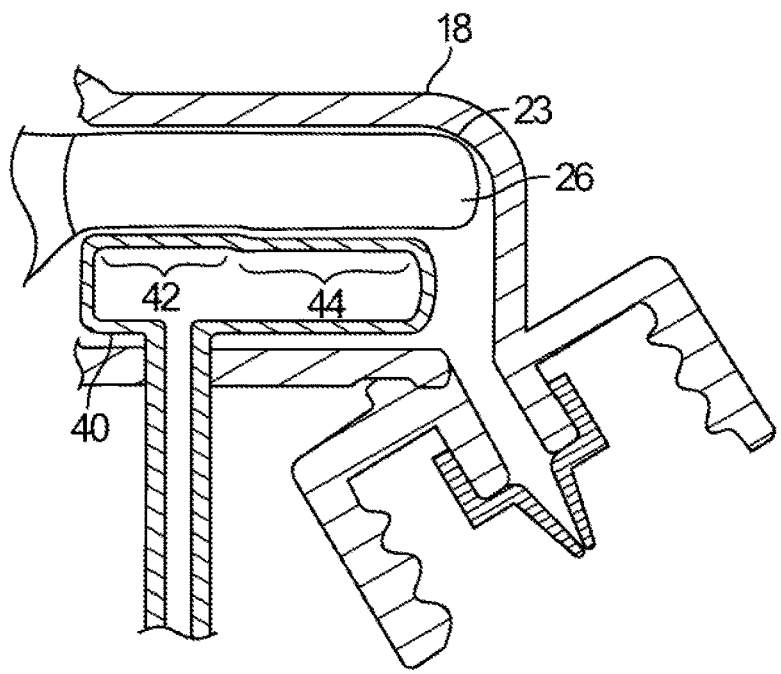
FIG. 5C is a cross section view of the first deformable elastic component of FIG. 4 in a fully inflated position, in accordance with embodiments of the present invention.

Referring to FIG. 5A, in an initial position, the first deformable elastic component 40 is fully deflated. Referring to FIG. 5B, in a slightly inflated configuration, the proximal section 42 of the first deformable elastic component 40 is expanded and moves up to asymmetrically compress the nipple 26. Referring to FIG. 5C, in a fully inflated position, the distal section 44 of the first deformable elastic component 40 is now fully up, uniformly compressing the nipple 26. When deflating from the fully inflated position of FIG. 5C, the first deformable elastic component 40 contracts asymmetrically to the slightly inflated position shown in FIG. 5B.

Figure 7:
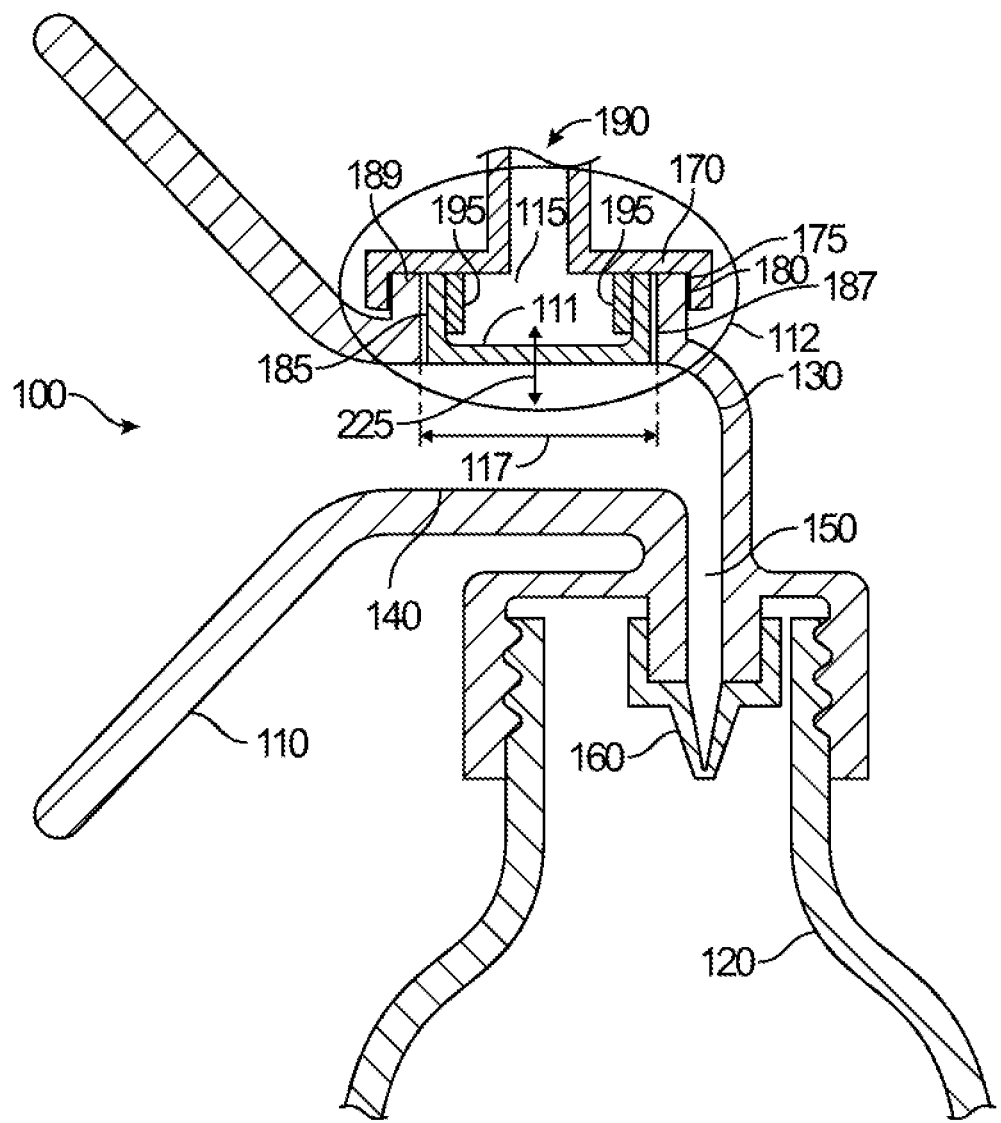
FIG. 7 shows a cross-sectional view of a breast pump head in accordance with an embodiment of the present invention, including a funnel-shaped breast shield section, a neck portion, a first deformable elastic capsule bonded at its sides into a pocket in the neck portion, a one-way valve, a breastmilk collection container.

An alternate design for a deformable elastic component, such as a bladder or an impermeable polymeric membrane, for use with a breast pump in accordance with the present invention is shown in FIG. 7. This deformable elastic component design can be used for either of the deformable elastic components 30, 40 described above and shown in the embodiments of FIGS. 1A-5C. Referring to FIG. 7, an assembled breast pump head for extracting breastmilk in accordance with the present invention is generally designated as reference numeral 100. The breast pump head 100 generally comprising an external shell that includes a funnel-shaped breast shield portion 110 configured to receive and seal against a breast (not shown in FIG. 7). As illustrated, the funnel-shaped breast shield portion 110 narrows and transitions to a roughly cylindrical and hollow neck portion 140 defining a proximal end located adjacent to the funnel-shaped breast shield portion 110 and a distal end positioned away from the funnel-shaped breast shield portion 110. The neck portion 140 is adapted to receive and position a nipple of the breast for extraction of breastmilk. Preferably, the distal end of the neck portion 140 is closed off, for example, by a distally curved portion 130, so that a channel is formed within the pump head 100 which feeds, at the distal end of the neck portion 140, to a feed channel 150. In operation, when a breast (not shown in FIG. 7) is placed in the pump head 100 to extract breastmilk, the breastmilk will feed through this feed channel 150, then though a one-way check valve 160 to be collected in a removable collection container 120, such as a baby bottle that can be topped off with a nipple for feeding an infant.

At least one deformable elastic membrane 111 is provided on the pump head 100 and adapted for alternating expansion and contraction to assist in milk extraction and help prevent nipple edema. The deformable elastic membrane 111 is positioned in an opening 117 with sidewalls 189 creating a pocket defined in the neck portion 140. As positioned in said opening 117, a first surface of the deformable elastic membrane 111 preferably extends across the opening 117 and faces the interior of the neck portion 140. The exterior sidewalls 185 of the deformable elastic membrane 111 are bonded to the interior sidewalls 187 of the pocket walls 189 that extend from the opening 117 in the neck portion 140. As illustrated in FIG. 7, a hermetic composite deformable elastic capsule 112 is disposed on the top surface of the neck portion 140 of the pump head 100. However, the hermetic composite deformable elastic capsule 112 could be located on a different portion of the neck portion 140, including coming up from the bottom surface, without departing from the spirit and principles of the present invention.

As with other embodiments described herein, the deformable elastic capsule 112 is generally hermetically sealed. While preferred embodiments utilize a unitary, hermetic bladder, as illustrated for other embodiments described herein, the deformable elastic capsule 112 can be constructed from multiple components, sealed together, that collectively define a composite construction composed of flexible elements (membrane 111) and rigid elements (sidewalls 189; plastic cap 170) bonded together so they function as a single hermetic unit. For example, the deformable elastic capsule 112 could comprise a hermetic composite capsule that defines a hermetic space, as illustrated in FIG. 7, adapted for movement under varying pressures, such as the procedures described herein. In alternate embodiments of the present invention, the deformable elastic capsule 112 can comprise a bladder, a hollow capsule, or the like, sealingly mounted relative to the opening 117 in the neck portion 140 of the pump head 100. In this regard, the deformable elastic capsule 112 may be hermetically bonded to the sidewalls 189 of the opening 117 so as to prevent leakage of breastmilk, or loss of suction or pressure from the interior of the pump head 100.

Referring again to FIG. 7, the deformable elastic membrane 111 includes a portion, illustrated as the bottom portion of the membrane 111, defining a first surface facing the interior of the neck portion 140. As further illustrated, deformable elastic membrane 111 has sidewalls, the exterior surfaces 185 of which being hermetically bonded to the interior surfaces 187 of the raised sidewalls 189 of the pocket that forms the opening 117 through the neck portion 140. To aid in bonding and in assembly, an internal form 195 can be provided to push outwards forcing the sidewalls of the deformable elastic membrane 111 out against the interior walls 187 of the raised sidewalls 189 of the pocket that forms the opening 117 through the neck portion 140.

In the embodiment of FIG. 7, the hermetic composite deformable capsule 112 is closed with a rigid top cover 170. The interior walls 175 of the rigid top cover 170 are bonded to the exterior sidewalls 180 of the pocket walls 189 that extend from the opening 117 in the neck portion 140.

The resultant "capsule" is hermetic but not unitary because it is not one piece. Instead, it is made of multiple pieces and so comprises a composite capsule. An interior space 115 of the hermetic composite deformable capsule 112, is preferably filled with an incompressible material, such as liquid, gel or the like, but which can also be filed with gas or air. In operation, the liquid, gel or other material is pumped into or out of the hermetic composite capsule through port 190 which connects by tubing to a pump motor unit. Alternately, the interior 155 can be filled with a gas or air which can be manipulated by a pump to expand or contract the deformable elastic capsule 112 under alternating applied positive and negative pressure.

In operation of the pump head 100, the breast (not shown in FIG. 7) is inserted into the funnel-shaped breast shield portion 110 and the nipple extends into the receiver neck portion 140. The deformable elastic capsule 112 is preferably in a relaxed state and allows the nipple to enter the neck portion 140 unimpeded. The funnel-shaped portion 110 preferably establishes a seal around the breast.

With the nipple so positioned, alternating positive and negative pressures are applied through the port 190 to the deformable elastic capsule 112, causing the interior surface of the deformable elastic membrane 111 to move toward or away from the interior axial center of the neck portion 140 (this motion being represented by arrow 225 in FIG. 7). For example, pumping fluid through the port 190 into the hermetic composite deformable capsule 112 and thereby increasing pressure inside the hermetic composite deformable capsule 112 will cause the deformable elastic membrane 110 to move toward the axial center of the neck portion 140. This will compress the nipple (not shown in FIG. 7) against the opposing interior solid surface (namely, bottom interior surface of the neck portion 140), thereby controlling nipple edema. Pumping fluid out of the port 190, thereby extracting it from the hermetic composite deformable capsule 112, will decrease pressure inside the hermetic composite deformable capsule 112. This will cause the deformable elastic membrane 110 to move away from the axial center of the neck portion 140. This will, in turn, create a volume within the neck portion 140, external to the deformable elastic membrane 111, around and in front of the nipple, to create suction and extract breastmilk. In FIG. 7, the in/out motion of the of the deformable elastic membrane 111 relative to the neck portion 140 is represented by arrow 225.

Referring to FIG. 6, a pump 61 actuated by a control panel 62 through a series of control electronics 64 is shown. While described hereinafter with reference to the pump head embodiment of FIGS. 1A-1B, the pump 61 and other operative components for expansion and contraction of the deformable elastic components can also be used with the deformable elastic component embodiments illustrated in FIG. 7.

The pump 61 includes a piston 66 housed within a cylinder 68. A motor 70 drives the piston 66 by a propulsion mechanism 71. The propulsion mechanism 71 can be, for example, lead screws, a rack and pinion system, a crank and axle system or other type of mechanism capable of extending and retracting the piston 66. In preferred embodiments of the present invention, the pump 61 is a hydraulic pump. In alternative embodiments, the pump 61 can be a pneumatic pump.

The pump 61 shown in FIG. 6 is a piston 66 in cylinder 68 although any positive displacement pump will suffice— e.g., a diaphragm pump, peristaltic pump, etc.

The control panel 62 includes an on/off switch 72, an MER button 73, a maximum MER pressure selector 74 and a maximum pump suction selector 76. The on/off switch 72 is configured to initiate the pump 61 through a series of control electronics 64 controlled by a control logic 83.

The pump 61 further includes an electrically actuated valve switch 84 to direct pump suction or pressure from the cylinder 68 to the second deformable elastic component 30 via the second pump tube 36 or to the first deformable elastic component 40 via the first pump tube 48. A reservoir 86 provides make-up liquid or air to the cylinder 68 of the pump 61. Similar to hydraulic and automotive braking systems, the pump 61 may further include an air bleed 88 to exhaust air in the case of a liquid-filled system, Alternating current (AC) or batteries 90 can provide power to the pump 61.

Position sensors, pressure sensors, stepper motors, and other suitable sensors and electronics may be included for controlling suction levels, suction rates, pumping frequency and the like, without departing from the scope of the present invention.

In embodiments, the pump 61 also includes a pressure sensor 92 connected to the cylinder 68 and adapted to report real-time system pressure to the control electronics 64.

In operation, the breast 14 is inserted into the breast shield section 12 and the nipple 26 extends into the receiver neck portion 18. The first deformable elastic component 40, which was fully deflated at the end of the last pumping session during the shutdown sequence, allows the nipple 26 to enter the nipple tunnel/receiver neck section 18 unimpeded. The location of the second deformable elastic component 30 and/or the funnel shape of the shield section 12 establish a seal around the breast 14.

Next, the pump 61 is switched on with the on/off switch 72 disposed on the control panel 62. The control electronics 64 start an initiation sequence by switching the valve switch 84 to the first deformable elastic component 40.

The activated pump 61 begins to cycle, alternately inflating and deflating the first deformable elastic component 40. With each deflation, suction in the receiver neck portion 18 increases, pulling/elongating the nipple 26. With each inflation of the first deformable elastic component 40, air in the receiver neck portion 18 is squeezed out through the check valve 22.

The initiation sequence continues until the nipple 26 contacts (i.e. is seated against) the downward curving portion 28.

At this point, the pressure sensor 92 will detect a sharp increase in suction when the nipple 26 seats against the downward curving portion 28 because the volume created by the downward motion of the first deformable elastic component 40 will no longer be absorbed by the nipple 26 pulling/elongating to fill that created volume. Upon detection, the pressure sensor 92 reports the abrupt suction increase to the control electronics 64 and control logic 83. The control logic 83 and control electronics 64 are pre-set to then switch the valve switch 84 to the second deformable elastic component 30 in response to this abrupt suction change report.

Next, the pump 61 and second deformable elastic component 30 initiate a stimulation phase by alternately expanding the second deformable elastic component 30 against the areola section of the breast 14 to cause compression and massage to that region. Such compression may be, for example, one hundred to one hundred forty compressions per minute, preferably one hundred twenty compressions per minute for approximately two minutes.

The second deformable elastic component 30 can be a bladder or other expandable membrane capable of expanding and contracting. In embodiments, the second deformable elastic component 30 is positioned such that the areolar region is contacted completely around its circumference by the second deformable elastic component 30. In some embodiments, only the top and bottom of the areolar region are contacted. In other embodiments, only the lower region of the areolar is contacted. Further, it is understood that the second deformable elastic component 30 can be disposed anywhere within the shield portion 12 or receiver neck portion 18, but preferably at transition region 20 and be bonded to some or the entire inner surface of the pump head 10, provided the second deformable elastic component 30 substantially performs the functions described herein.

The user may select the maximum MER pressure using knob 74 disposed on the control panel 62. A pressure feedback signal from the pressure sensor 92 allows for further fine-tuning pressure by the user. Inflation/deflation profiles are pre-programed.

The stimulation phase ends after expiration of a set time (e.g. two minutes) or by the user pressing the MER button 73. After the stimulation phase, an MER has likely been initiated.

The MER button 73 is a toggle, which may be selected any time during the pumping session causing a change from MER stimulation to milk extraction or vice versa.

This initiation sequence may alternatively be performed in reverse. That is, the second deformable elastic component 30 may operate first followed after two minutes or sooner if selected by the user, by the first deformable elastic component 40.

Additionally, the second deformable elastic component 30 and/or the first deformable elastic component 40 can be run under hot water to heat the components and any fluid contained therein. The warmth can also facilitate an MER.

After the preset time period or by the user pressing the MER button 73, the control electronics 64 cause the second deformable elastic component 30 to deflate, then cause the valve switch 84 to change back to the first deformable elastic component 40. The control electronics 64 then cause the first deformable elastic component 40 to inflate and deflate.

When the first deformable elastic component 40 begins to deflate, it creates volume around and in front of the nipple 26. The volume created by the deflation pulls the check valve 22 closed and creates suction, which extracts milk into the feed channel 21. More specifically, the extracted milk is drawn into the "suction chamber," a volume bounded by the nipple 26, the downward curving portion 28, the distal end of the second interface component 40 and the check valve 22. After air has been exhausted, the feed channel 21 is completely filled with liquid. In this regard, an important function of the one-way check valve 22 is to maintain separation between the liquid-filled feed channel 21 and the air-filled collection container 16 and, thereby, to maintain liquid fill in the pump head 10. This milk extraction process utilizing suction in a liquid-filled system mimics the natural suckling action of an infant.

When the first deformable elastic component 40 inflates two events occur. First, the nipple is compressed against the opposite solid surface in the receiver neck portion 18 squeezing the nipple tissues and thereby preventing edema, an accumulation of fluid in the tissues. Edema is a common cause of pain during breast pumping with conventional air-filled breast pumps which have no capability for nipple compression. This prevention of nipple edema by compression is analogous to the use of compression socks to control foot swelling from low pressure on airplanes. Second, as the first deformable elastic component 40 inflates, it moves toward the centerline of the receiver neck portion 18 causing a change from negative to positive pressure in the suction chamber. This positive pressure pushes the extracted milk through the check valve 22 and into the collection container 16.

In some embodiments, the surface of the first deformable elastic component 40 facing into the receiver neck portion 18 has a uniform thickness as shown in FIGS. 1A-18. In this case it inflates uniformly.

In alternative embodiments, the proximal section 42 of the surface of the first deformable elastic component 40 facing into the receiver neck portion 18 is thinner than the distal section 44, as shown in FIG. 4. Accordingly, when inflated, the more resilient proximal section 42 will rise in advance of the distal section 44. Conversely, when deflating, the proximal section 42 will fall later than the distal section 44. Thus, the proximal section 42 would lead on inflation and lag on deflation relative to the distal section 44.

The pump 61 actuates the piston 66 creating a pumping cycle of between forty and eighty, preferably about sixty cycles per minute. Maximum suction for the first deformable elastic component 40 can be controlled through feedback from the pressure sensor 92 and the separate maximum pump suction selector knob 76 disposed on the control panel 62. The suction rate curve to reach maximum suction caused by deflation of the first deformable elastic component 40 is pre-programed. Inflation/deflation frequency of the first deformable elastic component 40 is also pre-programmed or may be linked so that, for example, changing suction by knob 76 changes frequency in a pre-programmed fashion or frequency may be controlled by a separate knob 78 on the control panel 62.

When the pumping session is complete, the on/off switch 72 on control panel 62 is switched to the off position and a shutdown sequence is initiated. The valve switch 84 remains switched to the first deformable elastic component 40 until the first deformable elastic component 40 is fully deflated. Then the valve switch 84 switches to the second deformable elastic component 30, and fully deflates it. Control electronics 64 then switch off the pump 61 and the unit is fully off.

The user can insert a finger into the receiver neck section 18 and break the residual vacuum from the breast 14 and the shield portion 12.

Milk collected in the collection container 16 can be fed to an infant or stored for future use.

The leak-proof disconnects 38, 50 allow the pump head 10 to be separated from the tubes/nozzles coming from the pump 36, 48 without losing liquid from either part. After the leak-proof disconnects 38, 50 are separated; the pump head 10 can be cleaned. Alternatively, there may be no disconnects and the pump head 10 can be cleaned while still connected to the pump.

Additionally, the check valve 22 can be removed to facilitate cleaning the pump head 10. Any residual milk can be removed from the interior of the funnel portion 12 and the receiver neck portion 18 via a brush with soap, detergent and warm water.

One advantage of the bonding of the second deformable elastic component 30 and/or first deformable elastic component 40 to the hard shell of the pump head 10 is that the bonding holds the bladder in position and creates a liquid-tight seal. Thus, the pump head 10 of the present invention avoids breast milk leakage out of the receiver neck portion 18 and prevents extracted milk from collecting under the bladder. This feature also facilitates cleaning of the pump head assembly 10.

One advantage of a resilient proximal section 42 and the first deformable elastic component 40 is that the rise and fall motion is akin to a rolling action, allowing the proximal section 42 to "pine" the nipple 26 in place, restricting the nipple's elastic retraction away from the downward curving section 28 of the receiver neck section 18, when the first deformable elastic component 40 is deflated. Consequently, embodiments of the present invention may further limit ineffective nipple 26 motion that would dissipate suction.

One advantage of the first deformable elastic component 40 is to compress the nipple 26 against the opposite solid surface 23 in the receiver neck portion 18 with enough compressive force to prevent the pooling of blood and other fluids in the nipple 26 tissues. The compression helps prevent edema—painful condition caused by other commercially available suction-only breast pumps.

In embodiments solely using liquid to expand and contract the second deformable elastic component 30 and the first deformable elastic component 40, the pump 61 may deliver quicker and more precise actions and possibly with stronger force than can be achieved with air-filled systems.

Another advantage of the hydraulic embodiments is that the pump 61 may be physically smaller and the motor unit more discrete, as the hydraulic embodiments pump will pump less than five percent the volume per cycle when compared to air-driven pumps. Further, a less "hard working" pump can be quieter and more energy efficient, improving battery life, a great aid to mobility and ease of use.

Another advantage of the pump head 10 of the present invention is that expansion of the first deformable elastic component 40 reduces volume in the pumping cavity (i.e. receiver neck section 18) increasing pressure and forcing extracted milk through the check valve 22 and into the collection container 16. It is possible that this positive pressure will force milk through the check valve even when the user is lying down, a substantial advantage. Most commercial air-driven breast pumps can develop vacuum only with no ability to create positive pressure, and so they depend only on weight of the extracted breast milk to push it through the check valve. Pumping while lying down is not possible. This method does not work reliably, and milk often backs up into the vacuum line, sometimes contaminating the pump, and creating a very unhygienic condition.

In another embodiment the entire interior surface of pump head 10 may be coated with a highly elastic material to form an adherent membrane which covers the inside of funnel shield portion 12, neck portion 18, feed channel 21 and both the second deformable elastic component 30 and the first deformable elastic component 40. Such an elastic membrane allows full and unrestricted expansion and contraction functioning of both deformable elastic components while preventing milk collection in small spaces inside the pumping head. This configuration will ease cleaning.

Although generally described herein with reference to electric, hydraulic, pneumatic, and other "automatic" breast pumps, the present invention has utility with manual breast pumps without departing from the spirit and principles of the present invention. Additionally, the features of the present invention may also be used for milking machines. Specifically, the above described method and pump head 10 may be used for the milking of animals.

Although this invention has been shown and described with respect to the detailed embodiments thereof, it will be understood by those skilled in the art that various changes in form and detail thereof may be made without departing from the spirit and scope of the invention.

It is noted that the Figures are to be taken as an illustrative example only and are not to scale.

Additionally, it is also to be understood that the terminology used if for the purpose of describing particular embodiments only and is not intended to limit the scope of the claims of the present invention.

What is claimed is:
1. A device for extracting breastmilk from a breast, said device comprising:
   an external shell including:
      a funnel-shaped portion configured to receive and seal against the breast;
      a neck portion extending from the funnel-shaped portion and defining a proximal end and a distal end, said neck portion being adapted to receive and position a nipple of the breast, and
a feed channel defined at the distal end of the neck portion;
a one-way check valve disposed along the feed channel; and
a deformable elastic component having a surface facing into the neck portion, said deformable elastic component being adapted for alternating expansion and contraction;
wherein the deformable elastic component is configured to contract under applied negative pressure below the atmospheric pressure to create a volume external to the deformable elastic component, around and in front of the nipple, to create suction, elongate the nipple and extract breastmilk, and wherein the one-way check valve is closed by the suction so that extracted breastmilk collects in the feed channel; and
wherein the deformable elastic component is configured to expand tinder applied positive pressure above atmospheric pressure to compress the nipple against an opposing solid interior surface of the neck portion to control nipple edema, and wherein the expansion of the deformable elastic component pushes breastmilk through the one-way check valve.

2. The device according to claim 1, wherein the surface of the deformable elastic component facing into the neck portion is configured to move into an interior volume of the neck portion when positive pressure is applied to the deformable elastic component such that said surface of the deformable elastic component compresses the nipple against the opposing interior solid surface of the neck portion to control nipple edema, and
wherein the surface of the deformable elastic component facing into the neck portion is configured to move away from the interior of the neck portion when negative pressure is applied to the deformable elastic component so as to create a volume within the neck portion, external to the deformable elastic component, around and in front of the nipple, to create suction and extract breastmilk.

3. The device according to claim 1, wherein the surface of the deformable elastic component facing into the neck portion is shaped so that, without deflection, said surface and an interior surface of the neck portion adjacent thereto form a generally unobstructed cavity to receive and position the nipple of the breast.

4. The device according to claim 1, wherein the deformable elastic component comprises a hollow capsule sealingly mounted within an opening in the neck portion such that the surface faces inside the interior of the neck portion.

5. The device according to claim 1, further including a collection container attachable to the feed channel to receive extracted breastmilk, wherein the one-way check valve is disposed between the neck portion and the collection container to prevent air leakage from the collection container into the feed channel.

6. The device according to claim 1, wherein the negative and positive pressures are applied to the deformable elastic component by at least one of (i) a hydraulic pump operatively connected to the deformable elastic component; and (ii) an actuator mechanism operatively connected to the deformable elastic component.

7. The device according to claim 1, wherein the first deformable elastic component includes a proximal top surface and a distal top surface,
wherein the proximal top surface is more resilient than the distal top surface; and
wherein the proximal top surface rises in advance of the distal top surface when expanding and falls later than the distal top surface when contracting.

8. The device according to claim 4, wherein the capsule comprises a single unitary, hermetic unit.

9. The device according to claim 4, wherein the capsule is composed of multiple components sealed together and configured to function as a single unitary, hermetic unit.

10. The device according to claim 4, herein the capsule is filled with one of a liquid, a gel, or a gas.

11. The device according to claim 4, wherein the capsule is detachable from the neck portion.

12. The device according to claim 6, further comprising a second deformable elastic component adapted for alternating expansion and contraction for initiating a milk ejection reflex (MER) that is disposed at the junction of the funnel-shaped section and the neck portion of the external shell.

13. A device for extracting breastmilk from a breast, said device comprising:
an external shell including:
a funnel-shaped portion configured to receive and seal against the breast;
a neck portion extending from the funnel-shaped portion and defining a proximal end and a distal end, said neck portion being adapted to receive and position a nipple of the breast, and
a feed channel defined at the distal end of the neck portion;
a first deformable elastic component having a first surface facing into the neck portion, said first deformable elastic component being adapted for alternating expansion and contraction; and
a second deformable elastic component adapted for expansion and contraction and disposed within the device, said second deformable elastic component being configured to initiate a milk ejection reflex (MER);
wherein the first deformable elastic component is configured to contract under applied negative pressure below the atmospheric pressure to create a volume external to the first deformable elastic component, around and in front of the nipple, to create suction, elongate the nipple and extract breastmilk, and
wherein the first deformable elastic component is configured to expand under applied positive pressure above atmospheric pressure to compress the nipple against an opposing solid interior surface of the neck portion to control nipple edema.

14. The device according to claim 13, wherein the first surface of the first deformable elastic component facing into the neck portion is configured to move into an interior volume of the neck portion when positive pressure is applied to the first deformable elastic component such that said first surface of the first deformable elastic component compresses the nipple against the opposing interior solid surface of the neck portion to control nipple edema, and
wherein the first surface of the first deformable elastic component facing into the neck portion is configured to move away from the interior of the neck portion when negative pressure is applied to the first deformable elastic component so as to create a volume within the neck portion, external to the first deformable elastic component, around and in front of the nipple, to create suction and extract breastmilk.

15. The device according to claim 13, wherein the surface of the first deformable elastic component facing into the neck portion is shaped so that, without deflection, said first surface and an interior surface of the neck portion adjacent thereto form a generally unobstructed cavity to receive and position the nipple of the breast.

16. The device according to claim 13, wherein the first deformable elastic component comprises a hollow capsule sealingly mounted within an opening in the neck portion such that the inward-facing surface is contiguous with the inside surface of the neck portion.

17. The device according to claim 13, further comprising:
a collection container attachable to the teed channel to receive extracted breastmilk, and
a one-way check valve disposed between the neck portion and the collection container to prevent air leakage from the collection container into the feed channel.

18. The device according to claim 13, wherein the negative and positive pressures are applied to the first deformable elastic component by at least one of (i) a hydraulic pump operatively connected to the first deformable elastic component; and (ii) an actuator mechanism operatively connected to the first deformable elastic component.

19. The device ac co claim 16, wherein the capsule comprises a single unitary, hermetic unit.

20. The device according to claim 16, wherein the capsule is composed of multiple components sealed together and configured to function as a single unitary, hermetic unit.

21. The device according to claim 16, wherein the capsule is filled with one of a liquid, a gel, or a gas.

22. The device according to claim 16, wherein the capsule is detachable from the neck portion.

* * * * *

UNITED STATES PATENT AND TRADEMARK OFFICE
CERTIFICATE OF CORRECTION

| | | |
|---|---|---|
| PATENT NO. | : 11,147,905 B2 | Page 1 of 1 |
| APPLICATION NO. | : 17/060302 | |
| DATED | : October 19, 2021 | |
| INVENTOR(S) | : Carr Lane Quackenbush | |

It is certified that error appears in the above-identified patent and that said Letters Patent is hereby corrected as shown below:

In the Claims

Column 15, Line 21 – Claim 1, "tinder" should be "under"
Column 16, Line 11 – Claim 9, "herein" should be "wherein"
Column 17, Line 13 – Claim 17, "teed" should be "feed"

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*